(12) United States Patent
Han et al.

(10) Patent No.: US 11,278,569 B2
(45) Date of Patent: Mar. 22, 2022

(54) NATURAL KILLER CELL CONTAINING EXOGENOUS MITOCHONDRIUM AND PHARMACEUTICAL COMPOSITION COMPRISING SAME

(71) Applicant: PAEAN BIOTECHNOLOGY INC., Daejeon (KR)

(72) Inventors: Kyuboem Han, Daejeon (KR); Youngjun Lee, Seoul (KR)

(73) Assignee: PAEAN BIOTECHNOLOGY INC., Daejeon (KR)

( * ) Notice: Subject to any disclaimer, the term of this patent is extended or adjusted under 35 U.S.C. 154(b) by 360 days.

(21) Appl. No.: 16/349,310

(22) PCT Filed: Nov. 14, 2017

(86) PCT No.: PCT/KR2017/012883
§ 371 (c)(1),
(2) Date: May 13, 2019

(87) PCT Pub. No.: WO2018/088875
PCT Pub. Date: May 17, 2018

(65) Prior Publication Data
US 2019/0269731 A1    Sep. 5, 2019

(30) Foreign Application Priority Data

Nov. 14, 2016 (KR) ........................ 10-2016-0151411

(51) Int. Cl.

| | |
|---|---|
| *A61K 35/17* | (2015.01) |
| *A61P 35/02* | (2006.01) |
| *A61P 35/00* | (2006.01) |
| *C12N 5/078* | (2010.01) |
| *C12N 5/0783* | (2010.01) |
| *A61K 35/15* | (2015.01) |
| *A61K 9/19* | (2006.01) |
| *A61K 9/08* | (2006.01) |

(52) U.S. Cl.
CPC ................ *A61K 35/17* (2013.01); *A61K 9/08* (2013.01); *A61K 9/19* (2013.01); *A61K 35/15* (2013.01); *A61P 35/00* (2018.01); *A61P 35/02* (2018.01); *C12N 5/0634* (2013.01); *C12N 5/0646* (2013.01)

(58) Field of Classification Search
None
See application file for complete search history.

(56) References Cited

U.S. PATENT DOCUMENTS

2013/0034527 A1    2/2013    Hyde et al.
2015/0225697 A1    8/2015    Law et al.

FOREIGN PATENT DOCUMENTS

| KR | 1020140123503 A | 10/2014 |
|---|---|---|
| KR | 10-2015-0063374 A | 6/2015 |
| WO | 2013094988 A1 | 6/2013 |
| WO | 2015067089 A1 | 5/2015 |
| WO | 2016/008937 A1 | 1/2016 |
| WO | 2016/135723 A1 | 9/2016 |

OTHER PUBLICATIONS

Andrés Caicedo et al., "MitoCeption as a new tool to assess the effects of mesenchymal stem/stromal cell mitochondria on cancer cell metabolism and function", Scientific Reports, vol. 5, No. 1, Mar. 13, 2015, pp. 1-10 (10 pages total).
Andrés Caicedo et al., "Artificial Mitochondria Transfer: Current Challenges, Advances, and Future Applications," Stem Cells International, vol. 2017, Jul. 1, 2017, pp. 1-23 (23 pages).
Mi Jin Kim et al., "Delivery of exogenous mitochondria via centrifugation enhances cellular metabolic function", Scientific Reports, vol. 8, No. 1, Feb. 20, 2018, pp. 2-13 ( 13 pages total).
Kitani, T. et al.: "Internalization of Isolated Functional Mitochondria: Involvement of Macropinocytosis", Journal of Cellular and Molecular Medicine, vol. 18, No. 8, Jun. 2014 , pp. 1694-1703 (10 pages total).
Voigt J. et al., "Human natural killer cells acting as phagocytes against Candida albicans and mounting an inflammatory response that modulates neutrophil antifungal activity," JID, 2014, vol. 209, No. 4, pp. 616-626, p. 620 left col. bottom para, (11 pages total).
Tomoya Kitani, et al., "Internalization of isolated functional mitochondria: involvement of macropinocytosis", Journal of Cellular and Molecular Medicine, 2014, pp. 1694-1703, vol. 18, No. 8.
Korea Office Action for Application No. 10-2017-0151503 dated Mar. 13, 2018.
International Search Report for PCT/KR2017/012883 dated Feb. 14, 2018 [PCT/ISA/210].

*Primary Examiner* — Daniel C Gamett
(74) *Attorney, Agent, or Firm* — Sughrue Mion, PLLC

(57) ABSTRACT

An NK cells and PBMC, both having increased cytotoxicity are provided. Particularly, NK cells and PBMC which have exogenous mitochondria introduced thereinto potentiate the immune system of the human body to enhance a therapeutic effect on infectious diseases or cancer. Therefore, the NK cells and PBMC can be used in a composition for prevention or treatment of infectious diseases and cancer. Specially, autogenous NK cells and PBMC guarantee stability without the incurrence of an immune reaction, and thus would be expected to have high commercial activity.

14 Claims, 13 Drawing Sheets

Specification includes a Sequence Listing.

[FIG. 1]
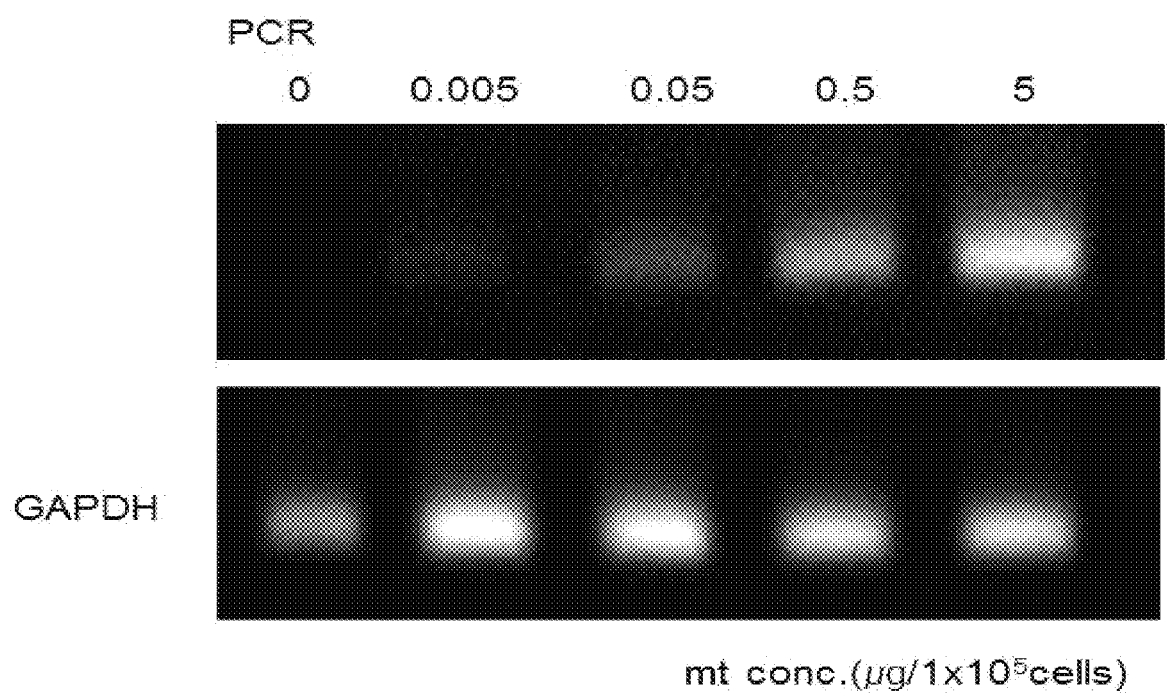

[FIG. 2]
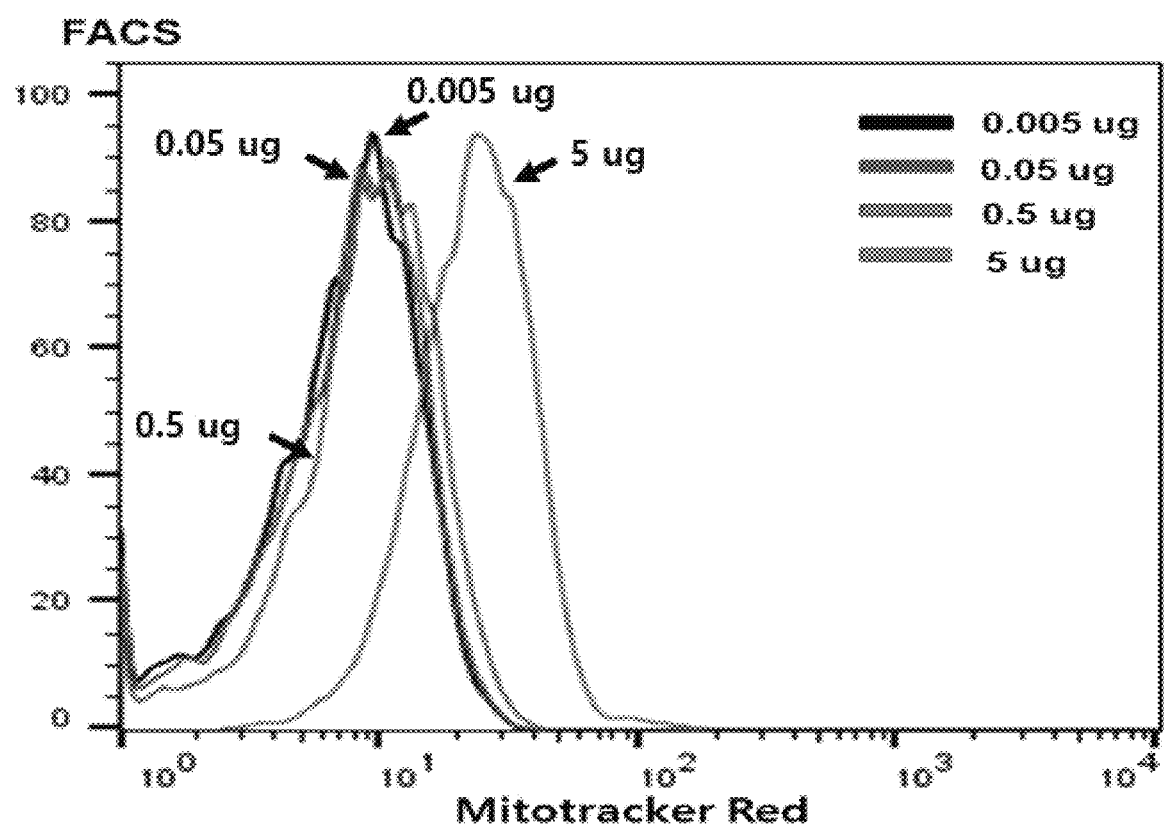

[FIG. 3]
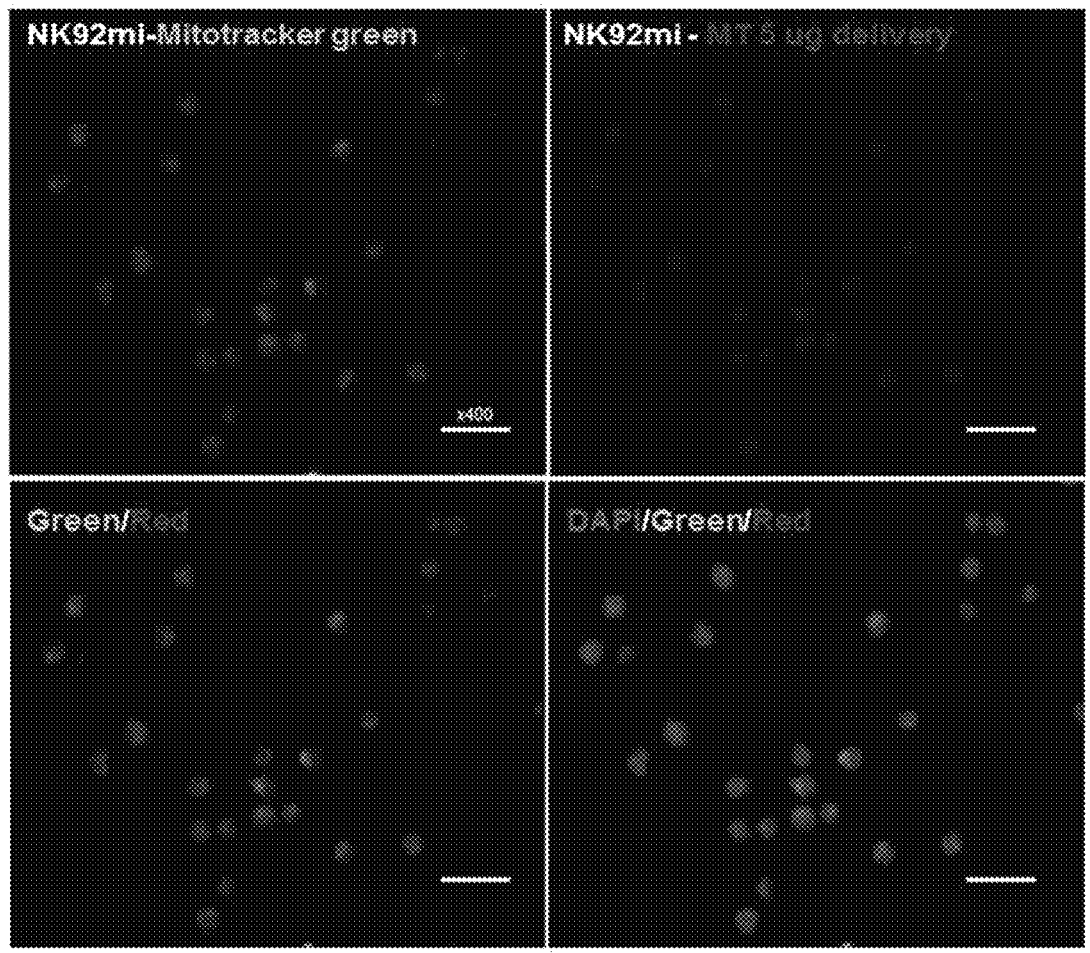

[FIG. 4A]
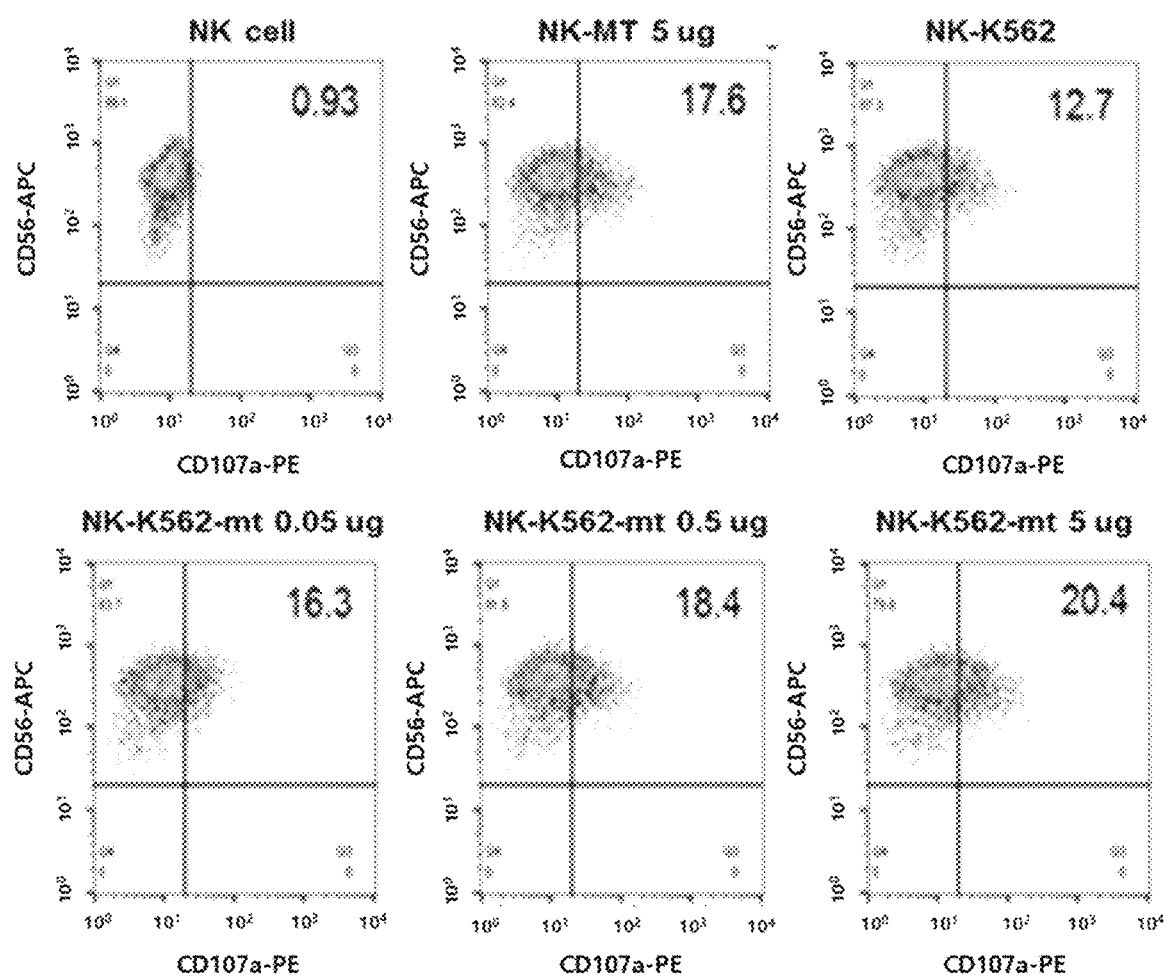

[FIG. 4B]
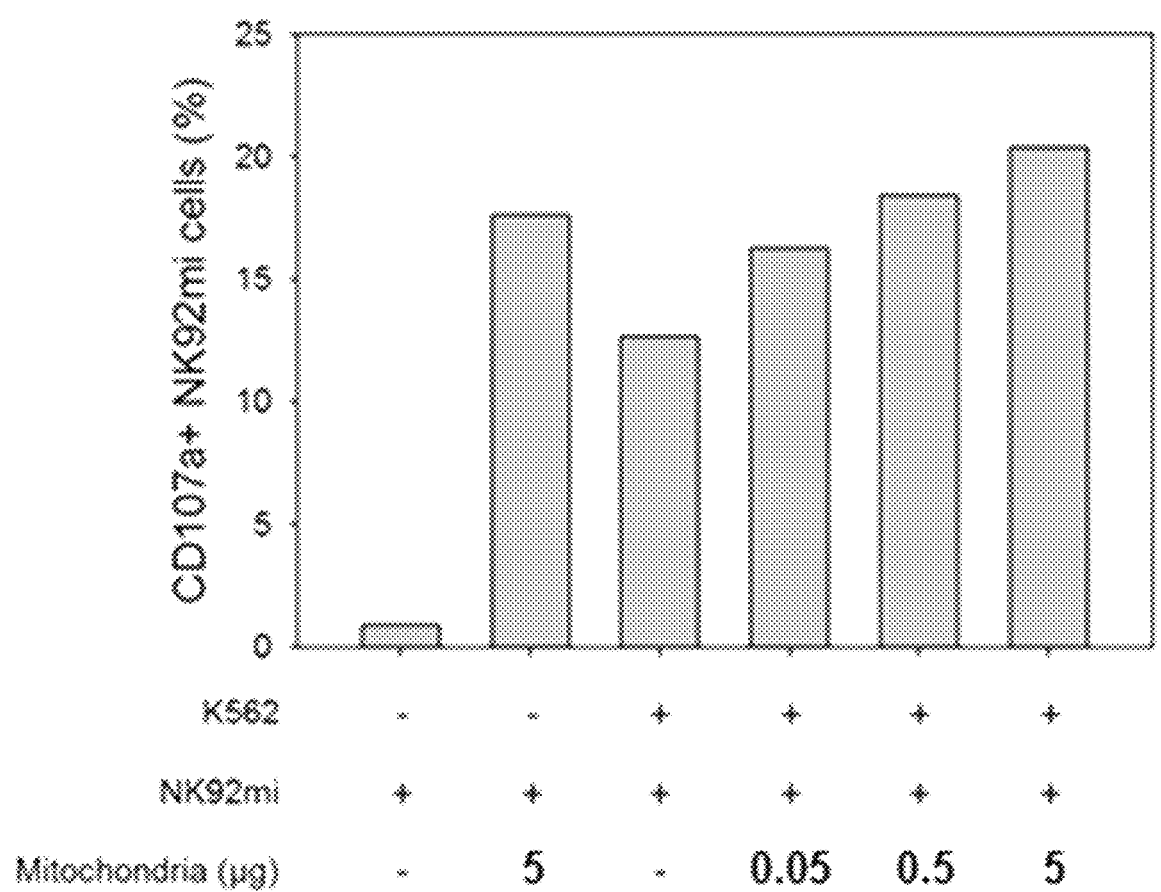

[FIG. 5]
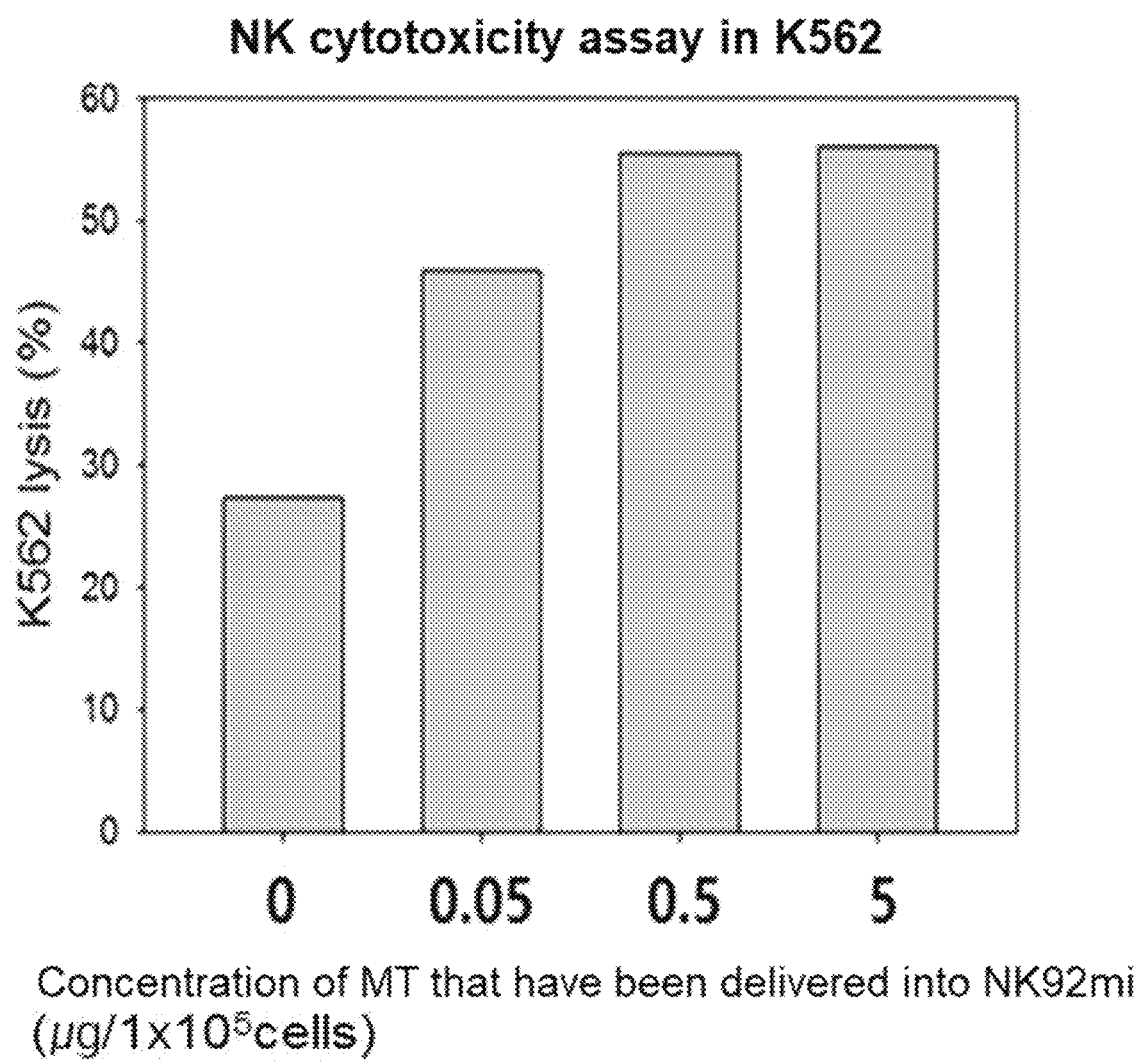

[FIG. 6]
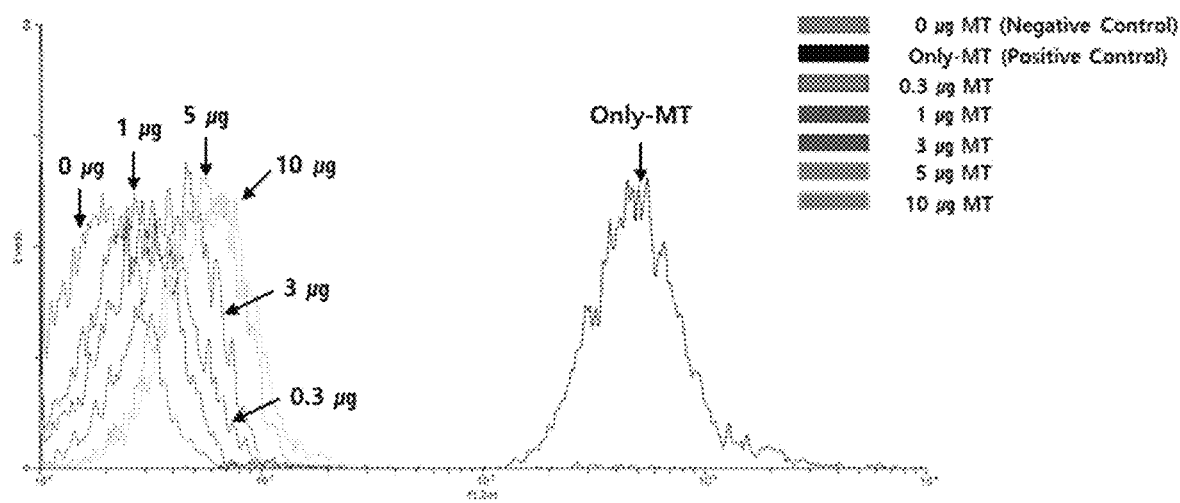

[FIG. 7]
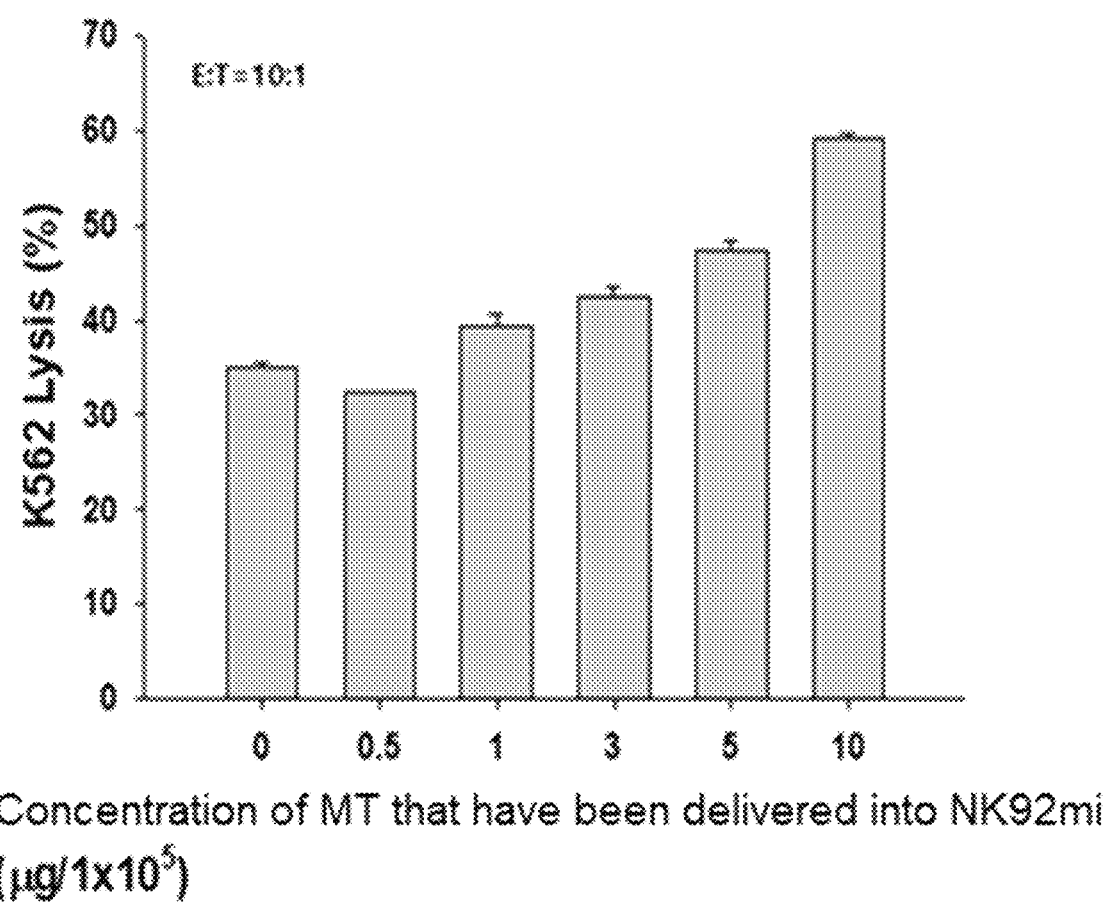

[FIG. 8A]
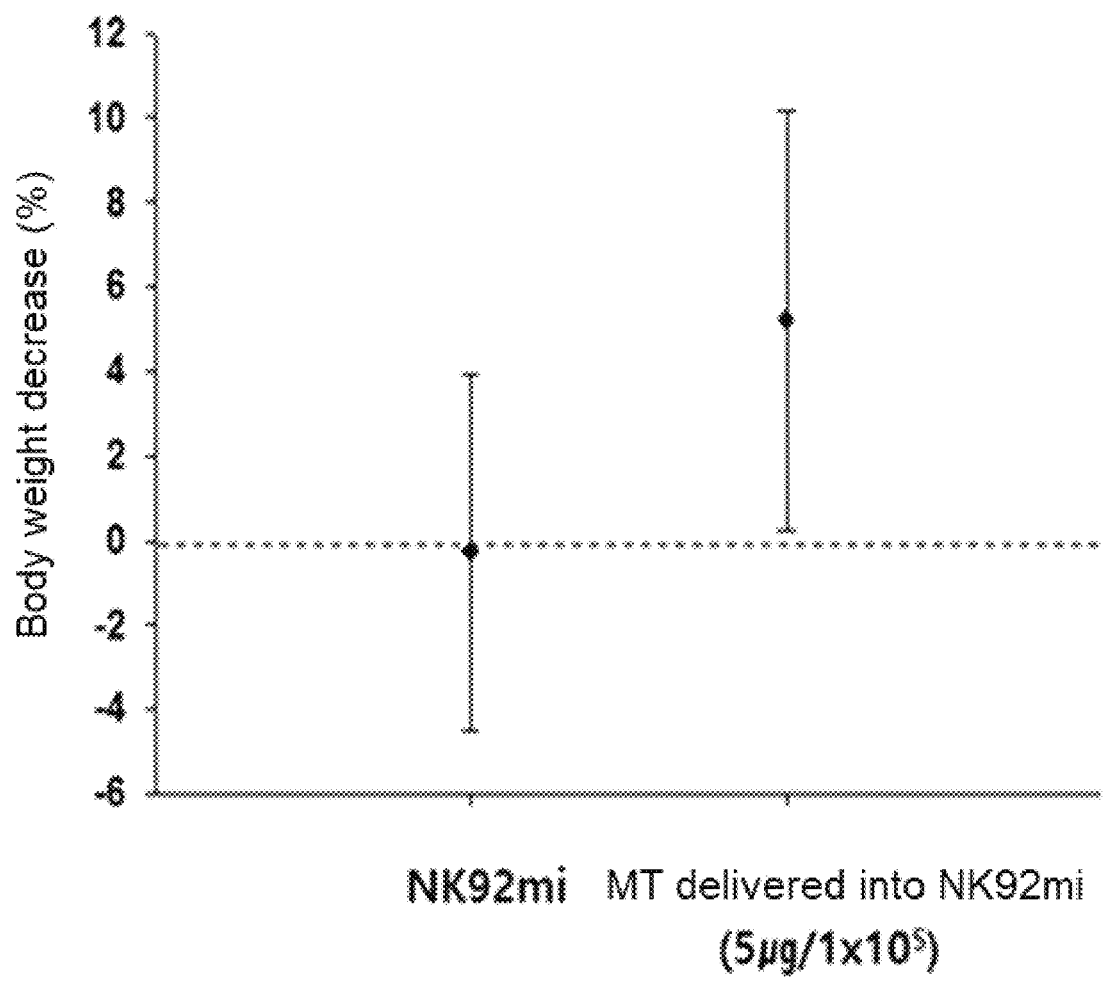

[FIG. 8B]
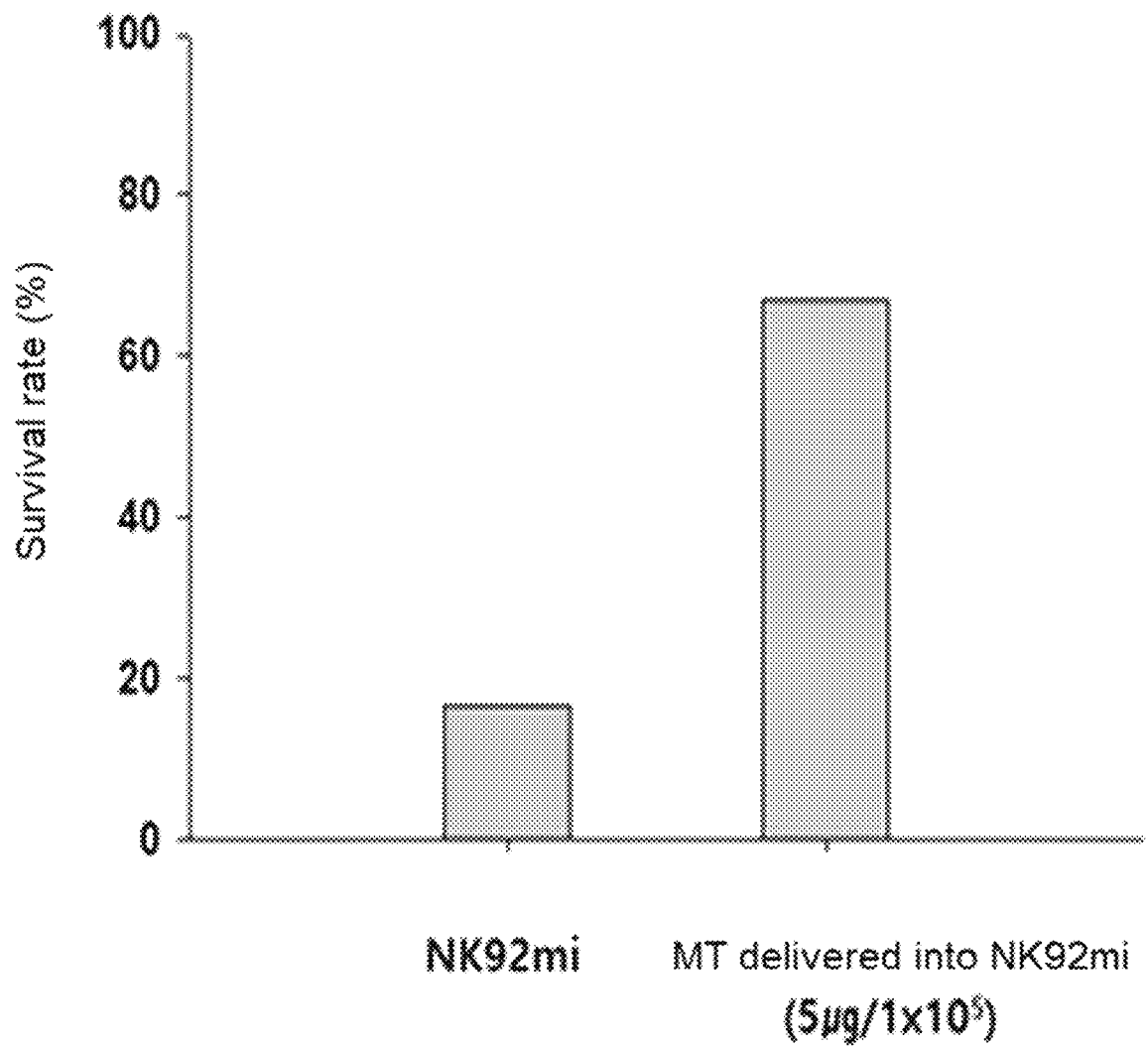

[FIG. 8C]
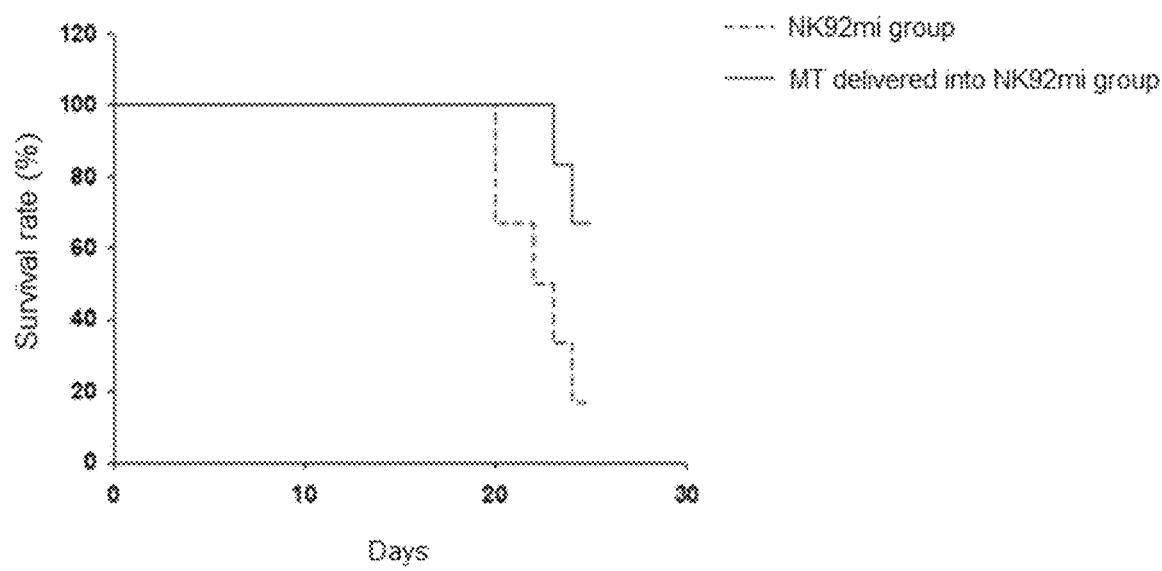

[FIG. 9]
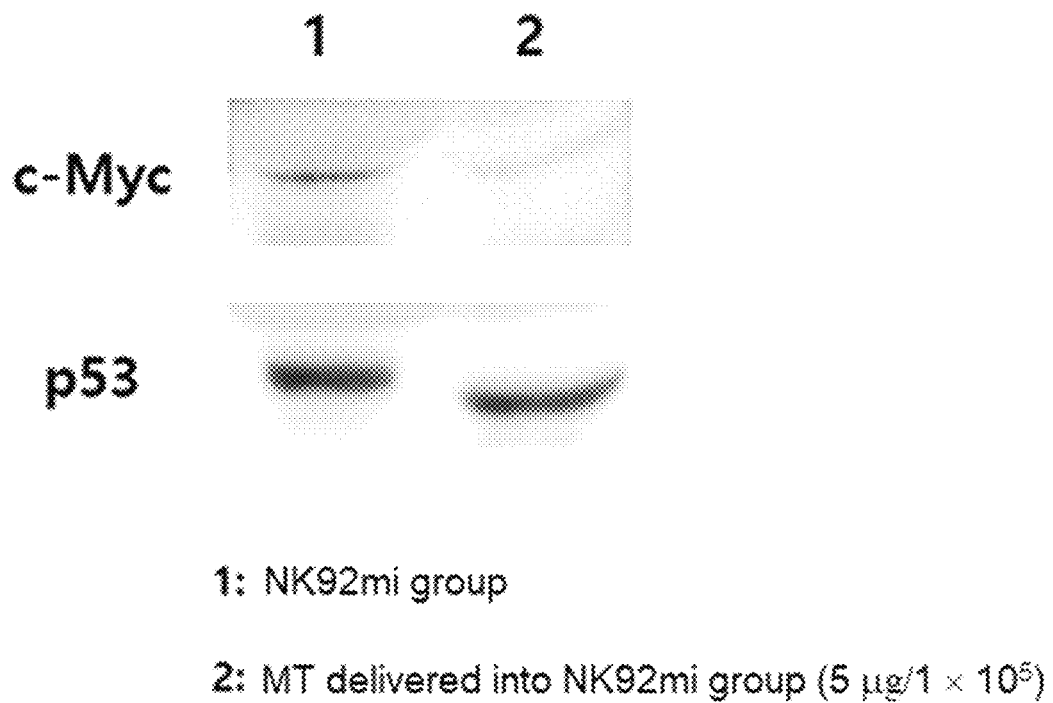
1: NK92mi group
2: MT delivered into NK92mi group (5 μg/1 × 10⁵)

[FIG. 10]
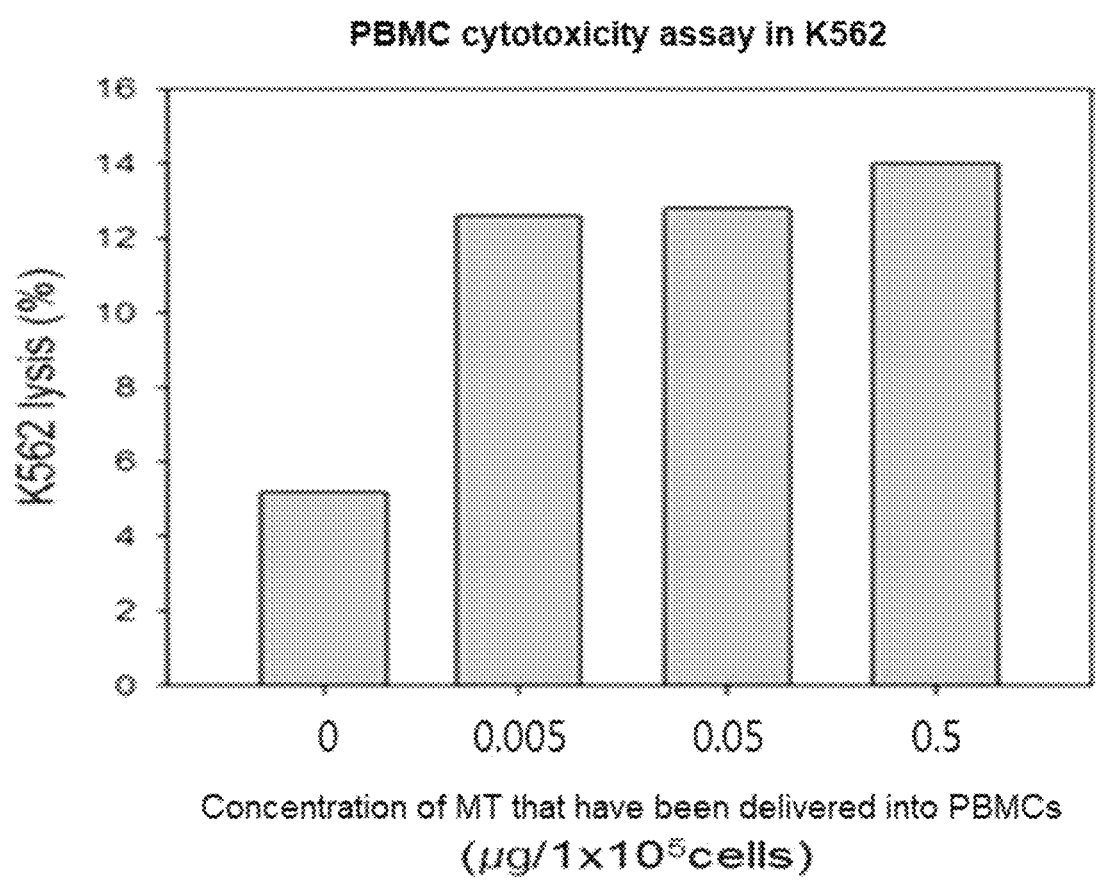

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Forward primer for detecting WRL-68
      mitochondria

<400> SEQUENCE: 1
ctattctctg ttctttcatg g                                           21

<210> SEQ ID NO 2
<211> LENGTH: 21
<212> TYPE: DNA
<213> ORGANISM: Artificial Sequence
<220> FEATURE:
<223> OTHER INFORMATION: Reverse primer for detecting WRL-68
      mitochondria

<400> SEQUENCE: 2
aagtatttat ggtaccgtac g                                           21

<210> SEQ ID NO 3
<211> LENGTH: 18
<212> TYPE: DNA
<213> ORGANISM: Artificial Sequence
<220> FEATURE:
<223> OTHER INFORMATION: Forward primer for detecting GAPDH gene

<400> SEQUENCE: 3
ggaaggtgaa ggtcggag                                               18

<210> SEQ ID NO 4
<211> LENGTH: 21
<212> TYPE: DNA
<213> ORGANISM: Artificial Sequence
<220> FEATURE:
<223> OTHER INFORMATION: Reverse primer for detecting GAPDH gene

<400> SEQUENCE: 4
ggcaacaata tccactttac c                                           21
```

NATURAL KILLER CELL CONTAINING EXOGENOUS MITOCHONDRIUM AND PHARMACEUTICAL COMPOSITION COMPRISING SAME

CROSS REFERENCE TO RELATED APPLICATIONS

This application is a National Stage of International Application No. PCT/KR2017/012883, filed on Nov. 14, 2017, which claims priority from Korean Patent Application No. 10-2016-0151411, filed on Nov. 14, 2016.

TECHNICAL FIELD

The present invention relates to a cell therapy products, and more particularly, to a natural killer (hereinafter referred to as NK) cell or a peripheral blood mononuclear cells (hereinafter referred to as PBMCs) which comprise exogenous mitochondria, and pharmaceutical compositions comprising the same as an active ingredient.

BACKGROUND ART

Recently, biopharmaceuticals have been developed to treat various incurable diseases. The biopharmaceuticals include protein drugs, antibody drugs and cell therapy products. Here, the cell therapy products refer to the pharmaceuticals used for the purpose of treatment, diagnosis, or prevention of diseases and the cell therapy products may be obtained through a series of actions such as by performing ex vivo isolation and proliferation or by altering biological characteristics of cells by other methods. The cell therapy products may come from autologous, allogeneic, or xenogeneic cells. Depending on the cell type, the cell therapy products can be categorized into somatic cell therapy products and stem cell therapy products.

On the other hand, immunotherapy using the patient's immune function has been paid attention in cancer therapy. In immunotherapy, properties of immune cells with diverse functions are utilized and cancer cells are eliminated through complex interactions of the immune cells. A PBMC in human blood is a blood cell with a round nucleus such as a lymphocyte or a monocyte, and includes B cells, T cells, macrophages, dendritic cells (DCs), and NK cells. Among them, NK and cytotoxic T lymphocytes (CTLs) cells directly eliminate cancer cells. Antigen-presenting cells that present antigens to these effector cells include dendritic cells or B cells. In addition, helper T cells and regulatory T cells which secrete various cytokines, and the like are involved in immune responses. Among these, NK cells are emerging and promising immune cells in immune cell therapies.

In particular, as NK cells have been shown to have an ability to kill cancer cells in a non-specific manner, many studies have been conducted on NK cells. Based on these researches, NK cell therapies in cancer, have been emerging tools for treatment of cancer cells. In particular, it has been reported that NK cells play an important role in innate and acquired immune responses achieved through cytokine secretion, against pathogens that have infected a host or cancer.

Accordingly, the present inventors have made efforts to find a new method for improving the power of cytotoxicity of NK cells and PBMCs. As a result, the present inventors have found a method of increasing the cytotoxicity of NK and PBMC, and thus provide a method of treating cancer using such cytotoxicity, and thus have completed the present invention.

Technical Problem

An object of the present invention is to provide an NK cell with increased cytotoxicity and a pharmaceutical composition comprising the same.

Another object of the present invention is to provide a PBMC with increased cytotoxicity and a pharmaceutical composition comprising the same.

Solution to Problem

In order to achieve the above objects, the present invention provides NK cells comprising exogenous mitochondria, and a pharmaceutical composition for preventing or treating cancer or an infectious disease, comprising the same.

In addition, the present invention provides PBMCs comprising exogenous mitochondria, and a pharmaceutical composition for preventing or treating cancer or an infectious disease, comprising the same.

Advantageous Effects of Invention

An NK cell and a PBMC, into which exogenous mitochondria have been introduced, not only have an increased cytotoxicity which results in increased cancer-specific killing effects, but also exhibit no side effects as immune cells existing in vivo. In addition, the NK cell and the PBMC are improved in terms of an ability of the cell itself, and thus can be widely applied to various diseases in which the NK cell and the PBMC are involved. As a result, it is expected that pharmaceutical compositions comprising the NK cell and the PBMC are highly commercially applicable.

BRIEF DESCRIPTION OF DRAWINGS

FIG. 1 illustrates a result obtained by a PCR analysis method in order to investigate whether human normal hepatocyte (WRL68)-derived mitochondria have been delivered into NK cells.

FIG. 2 illustrates a result obtained by FACS analysis in order to investigate whether human normal hepatocyte-derived mitochondria have been delivered into NK cells.

FIG. 3 illustrates results obtained by fluorescence microscopy, in order to locate the human normal hepatocyte-derived mitochondria delivered into NK cells.

FIGS. 4A and 4B illustrate results showing anti-cancer activity of NK cells into which exogenous mitochondria have been delivered by a CD107a degranulation assay.

FIG. 5 illustrates a result showing the cytotoxic effects of NK cells into which exogenous mitochondria have been delivered by K562 cytotoxicity assay.

FIG. 6 illustrates a result obtained by FACS analysis in order to investigate whether mitochondria derived from umbilical cord mesenchymal stem cells (UC-MSC) have been delivered into NK cells.

FIG. 7 illustrates a result showing the cytotoxic effects of NK cells into which UC-MSC-derived mitochondria have been delivered using K562 cytotoxicity assay.

FIGS. 8A to 8C illustrate results showing the therapeutic effects by NK cells, into which UC-MSC-derived mitochondria have been delivered in an animal model of acute myelogenous leukemia, in terms of body weight and survival rate of mice.

FIG. 9 illustrates results of expression distribution of blood tumor markers in an animal model of acute myelogenous leukemia which has been administered with NK cells into which UC-MSC-derived mitochondria have been delivered.

FIG. 10 illustrates a result showing the cytotoxic effects of PBMCs into which exogenous mitochondria have been delivered by K562 cytotoxicity assay

DETAILED DESCRIPTION OF INVENTION

Hereinafter, the present invention will be described in detail.

In an aspect of the present invention, there is provided an NK cell enriched by exogenous mitochondria.

As used herein, the term "exogenous mitochondria" refers to mitochondria introduced exogenously rather than mitochondria present in an NK cell. Here, the exogenous mitochondria may be obtained from the same subject as that from which the NK cell is obtained, but may be obtained from another subject. Here, the exogenous mitochondria may be obtained from a mammal, and preferably may be obtained from a human. For example, the exogenous mitochondria may be obtained from muscle cells, hepatocytes, fibroblasts, epithelial cells, neurons, adipocytes, osteocytes, leukocytes, lymphocytes, or mucosal cells, and preferably may be obtained from muscle cells with excellent mitochondrial activity. In addition, the mitochondria may be obtained from cells cultured ex vivo.

On the other hand, the exogenous mitochondria can be obtained by disrupting the cells and performing centrifugation, or by culturing the cells, disrupting the cells, and performing the centrifugation. For the method for obtaining mitochondria, a conventional method used for collecting an organelle can be used.

Here, an NK cell comprising exogenous mitochondria may be obtained by introducing mitochondria in an amount of 0.01 to 500 μg, 0.1 to 450 μg, 0.5 to 300 μg, 1 to 100 μg, or 2 to 10 μg, per $10^5$ NK cells. Here, an NK cell may contain 1 to $10^3$ or 10 to $10^2$ exogenous mitochondria. Specifically, the number of exogenous mitochondria may be such that approximately 1, 10, 100, or 500 exogenous mitochondria are contained in one NK cell. Here, the number of exogenous mitochondria contained in NK cells can be regulated by controlling an amount of exogenous mitochondria to be introduced into NK cells. Each subject NK cell may contain a different number of exogenous mitochondria.

In addition, the NK cells may be derived from a mammal or a human. Preferably, the NK cells may be obtained from a subject intended to receive NK cell therapy. Here, the NK cells may be directly isolated from the blood of the subject and used, or may be obtained by differentiating immature NK cells or stem cells obtained from the subject and used.

Meanwhile, in order to introduce the exogenous mitochondria into NK cells, the exogenous mitochondria and the NK cells may be mixed and then the mixture may be subjected to centrifugation so that the mitochondria are delivered efficiently into the NK cells. A condition at the time of performing centrifugation can be appropriately regulated to efficiently introduce the mitochondria without damaging the cells. Here, the centrifugation may be performed at room temperature, and a temperature condition can be appropriately selected for cell stability. Here, at the time of introducing the exogenous mitochondria, the NK cells and the exogenous mitochondria may be mixed in the presence of a surfactant so as to increase membrane permeability of the exogenous mitochondria into the NK cells, thereby increasing introduction efficiency of the exogenous mitochondria.

Here, the centrifugation may be performed at 100×g, 300×g, 500×g, 800×g, 1,000×g, 1,200×g, 1,500×g, 1,800×g, 2,000×g, 2,400×g, 3,000×g, 5,000×g, or 10,000×g. In addition, a centrifugation time may be 0.1 minutes to 60 minutes, but is not limited thereto. Specifically, the centrifugation time may be 1 minute, 2 minutes, 3 minutes, 5 minutes, 10 minutes, 20 minutes, or 30 minutes. In addition, the centrifugation may be performed at a temperature of 0° C. to 40° C., 20° C. to 38° C., or 30° C. to 37° C.

As such, by applying a centrifugal force to both the NK cells and the exogenous mitochondria, the mitochondria can be delivered into the NK cells with high efficiency while causing less damage to the NK cells.

In addition, a surfactant can be used to enhance cell membrane permeability of the exogenous mitochondria into the NK cells. A time point at which the surfactant is added may be before, during, or after mixing of the NK cells with the exogenous mitochondria. In addition, after the surfactant is added to the NK cells, the NK cells may be incubated for a certain period of time in order to increase the cell membrane permeability of the exogenous mitochondria into the NK cells. An incubation time may be 0.1 to 60 minutes. Specifically, the incubation time may be 1 minute, 5 minutes, 10 minutes, 20 minutes, or 30 minutes, but is not limited thereto.

Specifically, the surfactant is preferably a nonionic surfactant, and may be a poloxamer. Here, the poloxamer is a triblock copolymer composed of a central hydrophobic chain of polyoxypropylene flanked by two hydrophilic chains of polyoxyethylene. In addition, the surfactant in the mixture may have a concentration of 1 to 100 mg/ml, 3 to 80 mg/ml, or 5 to 40 mg/ml, and may be preferably 10 to 30 mg/ml.

In addition, the method may further comprise a step of incubating the mixture under a predetermined time and temperature condition. The incubation may be performed at a temperature of 0° C. to 40° C., 20° C. to 38° C., or 30° C. to 37° C. In addition, the incubation may be performed for 0.1 to 4 hours, 0.5 to 3.8 hours, or 0.8 to 3.5 hours. In addition, the incubation may be performed for a predetermined time after centrifugation is performed so as to deliver the exogenous mitochondria into the NK cells. In addition, the incubation time can be appropriately selected depending on a cell type and an amount of mitochondria.

In another aspect of the present invention, there is provided a pharmaceutical composition for treating cancer or an infectious disease, comprising, as an active ingredient, an NK cell that contains the exogenous mitochondria.

Here, the cancer may be any one selected from the group consisting of gastric cancer, liver cancer, lung cancer, colorectal cancer, breast cancer, prostate cancer, ovarian cancer, pancreatic cancer, cervical cancer, thyroid cancer, laryngeal cancer, acute myelogenous leukemia, brain tumor, neuroblastoma, retinoblastoma, head and neck cancer, salivary gland cancer, and lymphoma. In addition, the infectious disease may be any one selected from the group consisting of hepatitis B, hepatitis C, human papilloma virus (HPV) infection, cytomegalovirus infection, viral respiratory disease, and influenza.

In addition, the pharmaceutical composition may be made into a preparation in liquid or frozen form. Even in a case of being thawed again after freezing, the pharmaceutical composition does not exhibit impaired cellular function and can maintain high cell viability and cell-killing ability. Therefore, the pharmaceutical composition can be easily stored and supplied in a liquid- or frozen-stored form without additional processing.

In still another aspect of the present invention, there is provided a method for preventing or treating a disease, comprising a step of administering, to a subject, a pharmaceutical composition which contains, as an active ingredient, NK cells exogenous mitochondria.

Such a method comprises a step of administering an effective amount of the NK cell of the invention to a subject having a disease or a subject suspected of having a disease. For example, a cell into which exogenous mitochondria has been introduced can be administered to a subject, preferably a mammal, as a therapeutic preparation. The cell can be administered by an intravenous or subcutaneous route. In a case where the composition of the present invention is provided parenterally such as by intravenous, subcutaneous, ophthalmic, intraperitoneal, or intramuscular route, the composition is preferably in an aqueous form, or it is preferable that the composition includes a physiologically applicable body fluid, suspension, or solution. Accordingly, a carrier or vehicle is physiologically acceptable, and thus can be added to the composition and delivered to a patient. Such a carrier or vehicle does not adversely affect electrolyte of the patient. Therefore, physiological saline can be generally used as a carrier for preparations.

The method for preventing or treating a disease using the cell of the present invention may also comprise administering another drug or physiologically active substance having an effect of preventing or treating the disease, in combination with the cell of the present invention. A route, a time, and a dose for the combined administration can be determined depending on the type of disease, the patient's disease state, the purpose of treatment or prevention, and the other drug or physiologically active substance used in combination.

In addition, the disease may be cancer or an infectious disease. Here, the cancer may be selected from the group consisting of gastric cancer, liver cancer, lung cancer, colorectal cancer, breast cancer, prostate cancer, ovarian cancer, pancreatic cancer, cervical cancer, thyroid cancer, laryngeal cancer, acute myelogenous leukemia, brain tumor, neuroblastoma, retinoblastoma, head and neck cancer, salivary gland cancer, and lymphoma. The infectious disease may be any one selected from the group consisting of hepatitis B, hepatitis C, human papilloma virus (HPV) infection, cytomegalovirus infection, viral respiratory disease, and influenza.

In still yet another aspect of the present invention, there is provided PBMC comprising an exogenous mitochondria.

As used herein, the term "peripheral blood mononuclear cell" refers to a cell with a spherical nucleus present in the peripheral blood, which is referred to as peripheral blood monocyte or PBMC. Such PBMCs may include immune cells such as B cells, T cells, macrophages, dendritic cells, and NK cells. The PBMC can be obtained through the blood of a subject. Here, the exogenous mitochondria can be obtained from tissues or cells of the subject as described above.

Here, the PBMC comprising exogenous mitochondria may be obtained by introducing mitochondria in an amount of 0.01 to 500 μg, 0.1 to 450 μg, 0.5 to 300 μg, 1 to 100 μg, or 2 to 10 μg, per $10^5$ PBMCs. Here, the exogenous mitochondria may be contained in an amount of 1 to $10^3$ or 10 to 100, per one PBMC. In addition, a method of introducing the exogenous mitochondria into the PBMC can be carried out through centrifugation as described above. In still yet another aspect of the present invention, there is provided a pharmaceutical composition for treating cancer or an infectious disease, comprising, as an active ingredient, the PBMC that contains the exogenous mitochondria.

Here, as described above, the cancer may be selected from the group consisting of gastric cancer, liver cancer, lung cancer, colorectal cancer, breast cancer, prostate cancer, ovarian cancer, pancreatic cancer, cervical cancer, thyroid cancer, laryngeal cancer, acute myelogenous leukemia, brain tumor, neuroblastoma, retinoblastoma, head and neck cancer, salivary gland cancer, and lymphoma. In addition, the infectious disease may be any one selected from the group consisting of hepatitis B, hepatitis C, human papilloma virus (HPV) infection, cytomegalovirus infection, viral respiratory disease, and influenza.

Hereinafter, the present invention will be described in more detail with reference to the following examples. However, the following examples are provided only to illustrate the present invention, and the scope of the present invention is not limited only thereto.

I. Production of NK Cells into which Exogenous Mitochondria have been Introduced, and Identification of Functions Thereof Example 1. Production of NK Cells into which Exogenous Mitochondria have been Introduced Human normal hepatocytes (WRL-68) (CRL 1458, ATCC) were seeded in Dulbecco Modified Eagle Medium (DMEM) supplemented with 10% fetal bovine serum (FBS; Gibco), 100 μg/ml of streptomycin, and 100 U/ml of ampicillin and cultured for 72 hours. After completion of the culture, the cells were washed twice with Dulbecco Phosphate Buffered Saline (DPBS; Gibco). The washed cells were treated with 0.25% trypsin-EDTA (TE; Gibco) to obtain cells. For the obtained cells, in order to extract mitochondria, a hemocytometer was used to measure the number of cells, and cells in an amount of about $3 \times 10^6$ cells/ml were collected.

Thereafter, the cell line was subjected to primary centrifugation at a temperature of about 4° C. for 10 minutes with a speed of 350×g. The resulting pellet was collected, and resuspended and homogenized in a buffer solution for 10 to 15 minutes. A composition containing the pellet was subjected to secondary centrifugation at a temperature of about 4° C. for 3 minutes with a speed of 1,100×g, to obtain supernatant. Then, the supernatant was subjected to tertiary centrifugation at a temperature of about 4° C. for 15 minutes with a speed of 12,000×g, to isolate mitochondria from the cell line.

The isolated mitochondria were injected, in an amount of $1 \times 10^5$, into a test tube containing separate human NK cells (NK92mi) (CRL2408; ATCC), and centrifugation was performed at a temperature of about 4° C. for 15 minutes with a speed of 2,500×g. After removal of supernatant, washing with PBS was performed and centrifugation was performed at a temperature of about 4° C. for 5 minutes. Washing was performed twice under the same condition. Here, the isolated mitochondria were delivered at weights of 0.05, 0.05, 0.5, and 5 μg, per $1 \times 10^5$ recipient cells.

Example 2. Identification of Delivery of Human Normal Hepatocyte (WRL68)-Derived Mitochondria into NK Cells (PCR Analysis Method)

A DNA purification kit (NucleoSpin; MACHEREY-NA-GEL GmbH & Co. KG) was used to extract the entire gene from the NK cells collected in Example 1. The extracted DNA was respectively mixed with WRL-68 mitochondria-specific identification primers (F: 5'-CTA TTC TCT GTT CTT TCA TGG-3' (SEQ ID NO: 1), R: 5'-AAG TAT TTA TGG TAC CGT ACG-3' (SEQ ID NO: 2)). Then, the 2×PCR Master Mix (Applied Biosystems, Foster City, Calif., USA) and tertiary distilled water were added so that a total volume of the resultant was made 10 µl, and the Veriti 96-well Thermal Cycler (Applied Biosystems) was used to amplify a desired DNA portion.

A PCR reaction was performed to obtain amplified DNA. In order to identify the amplified DNA, electrophoresis on a 1.5% agarose gel was performed, and then staining with Loading Star (DYNEBIO INC., Seongnam, Korea) was performed. A UV-spectrometer (Chemi-Doc XRS; Bio-Rad Laboratories, Inc., Hercules, Calif., USA) was used to identify amplified DNA bands. GAPDH was selected as a house keeping gene. For this, primers (F-5'-GGA AGG TGA AGG TCG GAG-3' (SEQ ID NO: 3), R-5'-GGC AAC AAT ATC CAC TTT ACC-3' (SEQ ID NO: 4)) capable of amplifying GADPH were used. This result is illustrated in FIG. 1.

FIG. 1 indicated that an amount of the exogenous mitochondria delivered into the NK cells is increased as amounts (0.005, 0.05, 0.5, and 5 µg) of the mitochondria to be mixed with the NK cells are increased.

Example 3. Identification of Delivery of Human Normal Hepatocyte (WRL68)-Derived Mitochondria into NK Cells (FACS Analysis Method)

Fluorescence-activated cell sorter (FACS) analysis was performed to identify whether hepatocyte-derived mitochondria had been delivered into NK cells. The mitochondria isolated from human normal hepatocytes were treated with 500 nM Green mitotracker (Thermo Fisher Scientific, Waltham, USA). The resultant was allowed to react for 10 minutes in a 5% $CO_2$ incubator at 37° C., and washed. The fluorescence-labeled mitochondria derived from hepatocytes were delivered into immune cells using a centrifugation method, and then the immune cells were resuspended in 1 mL of PBS. Then, the mitochondrial delivery was identified and analyzed using the FACS Calibur flow cytometer (BDBiosciences, San Jose, Calif., USA). The result is illustrated in FIG. 2.

From FIG. 2, it was identified that the NK cells can be distinguished depending on amounts (0.005, 0.05, 0.5, and 5 µg) of the mitochondria delivered into the NK cells.

Example 4. Identification of Delivery of Human Normal Hepatocyte (WRL68)-Derived Mitochondria into NK Cells (Observation with Fluorescence Microscopy)

In order to identify whether normal hepatocyte (WRL-68)-derived mitochondria had been delivered into human NK cells (NK92mi), mitochondria of the NK cells were treated with 500 nM Green mitotracker (Thermo Fisher Scientific, Waltham, USA), and allowed to react for 10 minutes in a 5% $CO_2$ incubator at 37° C. The isolated mitochondria of the hepatocytes were treated with 500 nM red mitotracker. The resultant was allowed to react for 10 minutes in a 5% $CO_2$ incubator at 37° C., and then delivered into NK cells. After 5 µg of the mitochondria was delivered, the resultant was seeded in a 24-well plate and incubated in a 5% $CO_2$ incubator at 37° C. Then, fluorescence microscopy was used to identify intracellular delivery within 24 hours. A DAPI reagent for nuclear staining was used as a control staining reagent. The results are illustrated in FIG. 3.

From FIG. 3, it was identified that the exogenous mitochondria had been delivered into the NK cells.

Example 5. Analysis of Changes in Anti-Cancer Activity of NK Cells into which Mitochondria have been Delivered (CD107a Degranulation Assay)

In the human NK cells (NK92mi) collected in Example 1, into which exogenous mitochondria had been introduced, in order to identify expression of CD107a due to degranulation which is an indicator for NK cell activity, the human NK cells and target cells (K562) were mixed at a ratio of 10:1, and then the mixture was treated with fluorescent material-conjugated anti-CD107a. The resultant was co-incubated for 4 hours. After the co-incubation, the resultant was treated with anti-CD56 for surface staining and allowed to react for 30 minutes. Then, fluorescence-activated cell sorter (FACS) analysis was performed. The results are illustrated in FIGS. 4A and 4B.

From FIGS. 4A and 4B, it was identified that anti-cancer activity of the NK cells is increased with amounts (0.05, 0.5, and 5 µg) of the exogenous mitochondria.

Example 6: Identification (K562 Cytotoxicity Assay) of Changes in Anti-Cancer Activity of NK Cells into which Mitochondria have been Delivered In order to identify anti-cancer activity of the NK cells collected in Example 1, the collected NK cells were mixed, at 10:1, with target cells (K562) labeled with green fluorescence staining (CFSE; Invitrogen), and then the mixture was co-incubated for 4 hours in an incubator with a condition of 5% $CO_2$ at 37° C. After the co-incubation, in order to analyze the target cells killed by the NK cells, the resultant was treated with red fluorescence staining (7-AAD; Invitrogen), and then allowed to react for 10 minutes. Fluorescence intensity of the killed target cells was analyzed with fluorescence-activated cell sorter (FACS). The result is illustrated in FIG. 5.

From FIG. 5, it was identified that cytotoxicity against K562 is increased with amounts (0.05, 0.5, and 5 µg) of the delivered exogenous mitochondria.

Example 7. Production of NK Cells into which Mitochondria of Umbilical Cord-Derived Mesenchymal Stem Cells have been Introduced Placenta (provided by CHA bundang medical center, IRB No. 1044308-201511-BR-022-02)-derived mesenchymal stem cells were seeded in Alpha-Minimum Essential Medium (Alpha-MEM) supplemented with 10% fetal bovine serum (FBS; Gibco), 100 µg/ml of streptomycin, and 100 U/ml of ampicillin, and cultured for 72 hours.

After completion of the culture, the cells were washed twice with Dulbecco Phosphate Buffered Saline (DPBS; Gibco). The washed cells were treated with 0.25% trypsin-EDTA (TE; Gibco) to obtain cells. For the obtained cells, in order to extract mitochondria, a hemocytometer was used to measure the number of cells, and cells in an amount of about $2 \times 10^7$ cells/ml were collected.

Thereafter, the cell line was subjected to primary centrifugation at a temperature of about 4° C. for 10 minutes with a speed of 350×g. The resulting pellet was collected, and resuspended and homogenized in a buffer solution for 10 to 15 minutes. A composition containing the pellet was subjected to secondary centrifugation at a temperature of about 4° C. for 3 minutes with a speed of 1,100×g, to obtain supernatant. Then, the supernatant was subjected to tertiary centrifugation at a temperature of about 4° C. for 15 minutes with a speed of 12,000×g, to isolate mitochondria from the cell line.

The isolated mitochondria were injected, in an amount of $1 \times 10^5$, into a test tube containing separate human NK cells (NK92mi) (CRL2408; ATCC), and centrifugation was performed at a temperature of about 4° C. for 15 minutes with a speed of 2,500×g. After removal of supernatant, washing with PBS was performed and centrifugation was performed at a temperature of about 4° C. for 5 minutes. Washing was performed twice under the same condition. Here, the isolated mitochondria were delivered at weights of 0.3, 1, 3, 5, and 10 μg, per $1 \times 10^5$ recipient cells.

Example 8. Identification of Delivery of Mitochondria of Umbilical Cord-Derived Mesenchymal Stem Cells (UC-MSCs) into NK Cells (FACS Analysis Method)

Fluorescence-activated cell sorter (FACS) analysis was performed to identify whether mitochondria derived from umbilical cord-derived mesenchymal stem cells had been delivered into NK cells. Mitochondria isolated from the umbilical cord-derived mesenchymal stem cells were treated with 500 nM Red mitotracker (Thermo Fisher Scientific, Waltham, USA). The resultant was allowed to react for 30 minutes in a 5% $CO_2$ incubator at 37° C. and washed. The fluorescence-labeled mitochondria of the umbilical cord-derived mesenchymal stem cells were delivered into immune cells using a centrifugation method, and then the cells were resuspended in 1 mL of PBS. Then, the mitochondrial delivery was identified and analyzed using the FACS Calibur flow cytometer (BDBiosciences, San Jose, Calif., USA). The results are illustrated in FIG. 6.

From FIG. 6, it was identified that the NK cells can be distinguished with amounts (0.3, 1, 3, 5, and 10 μg) of the UC-MSC-derived mitochondria which have been delivered into the NK cells.

Example 9. Identification of Changes in Anti-Cancer Activity of NK Cells into which Mitochondria Derived from Umbilical Cord-Derived Mesenchymal Stem Cells (UC-MSCs) have been Delivered (K562 Cytotoxicity Assay)

In order to identify anti-cancer activity of the NK cells collected in Example 7, the collected NK cells were mixed, at 10:1, with target cells (K562) labeled with green fluorescence staining (CFSE; Invitrogen), and then the mixture was co-incubated for 4 hours in an incubator with a condition of 5% $CO_2$ at 37° C. After the co-incubation, in order to analyze the target cells killed by the NK cells, the resultant was treated with red fluorescence staining (7-AAD; Invitrogen), and allowed to react for 10 minutes. Fluorescence intensity of the killed target cells was analyzed with fluorescence-activated cell sorter (FACS). The results are illustrated in FIG. 7.

From FIG. 7, it was identified that cytotoxicity against K562 is increased with amounts (0.5, 1, 3, 5, and 10 μg) of the delivered exogenous mitochondria.

Example 10. Identification of Therapeutic Evaluation on Acute Myelogenous Leukemia Through Body Weight Change and Survival Rate 6- to 8-week-old male NOD.cg-Prkdcscid IL2rgtm1Sug/JicKoat mice were purchased from Koatech Co., Ltd. (Gyeonggi-do, Korea). The purchased mice were subjected to an adaptation period in a clean zone of the experimental animal center at the CHA University, and then an experiment was conducted. During the adaptation period, the environment in which the mice are kept had day and night at a 12-hour interval, and was maintained at a room temperature of 23±2° C. and a humidity of 40% to 60%. The mice were subjected to such an adaptation period for 7 days, and then put into the experiment. The mice thus prepared were administered, via the tail vein (intravenous (i.v.) injection), K562 cells in an amount of $2 \times 10^5$ cells/100 μl, so that an acute myelogenous leukemia model was produced.

Here, mice in which acute myelogenous leukemia had been induced were administered, via the tail vein (intravenous (i.v.) injection), the NK cells (NK92mi) prepared according to Example 7 in an amount of $2 \times 10^6$ cells/100 μl, so that an experimental group was produced. In the same manner, a control group was produced by administration of normal NK cells (NK92mi), into which the mitochondria had not been delivered, in an amount of $2 \times 10^6$ cells/100 μl. Body weight change and survival rate of the experimental group and the control group were analyzed for 24 days from a time point at which the acute myelogenous leukemia cell line (K562) had been administered. The results are illustrated in FIGS. 8A to 8C.

From FIGS. 8A to 8C, it was identified that the group, which has been administered the NK cells into which the mitochondria of the umbilical cord-derived mesenchymal stem cells were delivered, exhibits an about 5% increase in body weight and an about 40% or more increase in survival rate, as compared with the group which has been administered the normal NK cells into which the mitochondria of the umbilical cord-derived mesenchymal stem cells were not delivered.

Example 11. Identification of Therapeutic Evaluation on Acute Myelogenous Leukemia Through Analysis of Tumor-Associated Markers In order to identify expression distribution of the tumor-associated markers, p53 and c-Myc, the blood of the experimental group and the control group to which an experiment had been conducted according to Example 10 was collected, and then centrifuged at 12,000×g for 15 minutes to isolate the serum. The isolated serum was analyzed for expression distribution of p53 and c-Myc using the Western Blot Kit (WB; Bio-Rad Laboratories, Inc.). The results are illustrated in FIG. 9.

From FIG. 9, it was identified that the group, which has been administered the NK cells into which the mitochondria derived from the umbilical cord-derived mesenchymal stem cells were delivered, exhibits decreased expression of c-Myc and increased expression of p53, the c-Myc and p53 being blood tumor markers.

II. Production of PBMCs into which Exogenous Mitochondria have been Introduced and Identification of Functions Thereof

Example 12. Production of PBMCs into which Exogenous Mitochondria have been Introduced The peripheral blood of the inventor which had been taken by a clinician (at CHA medical center) was treated with Ficoll-Paque (Amersham Biosciences) at 1:1 in a Falcon tube, and then the resultant was subjected to centrifugation at 400×g for 35 minutes, to collect a PBMC pellet. The collected PBMCs were washed twice with PBS. Then, the human hepatocyte (WRL-68)-derived mitochondria which had been isolated according to Example 1 were delivered into the PBMCs at weights of 0.05, 0.05, 0.5, and 5 μg, per $1\times10^5$ recipient cells.

Example 13. Identification of Changes in Anti-Cancer Activity of PBMCs into which Mitochondria have been Delivered (K562 Cytotoxicity Assay)

In order to identify anti-cancer activity of the PBMCs collected in Example 12, the collected PBMCs were mixed, at 10:1, with target cells (K562) labeled with green fluorescence staining (CFSE; Invitrogen), and then the mixture was co-incubated for 4 hours in an incubator with a condition of 5% $CO_2$ at a temperature of 37° C. After the co-incubation, in order to analyze the target cells killed by the NK cells, the resultant was treated with red fluorescence staining (7-AAD; Invitrogen), and then allowed to react for 10 minutes. Fluorescence intensity of the killed target cells was analyzed with fluorescence-activated cell sorter (FACS). The result is illustrated in FIG. 10.

From FIG. 10, it was identified that cytotoxicity against K562 is increased with amounts (0.005, 0.05, and 0.5 μg) of the delivered exogenous mitochondria.

The invention claimed is:

1. A natural killer cell, comprising exogenous mitochondria.

2. The natural killer cell of claim 1, wherein the exogenous mitochondria are obtained from muscle cells, hepatocytes, fibroblasts, epithelial cells, neurons, adipocytes, osteocytes, leukocytes, lymphocytes, stem cells, or mucosal cells.

3. The natural killer cell of claim 1, wherein the exogenous mitochondria are contained in an amount of 1 to $10^3$ per natural killer cell.

4. The natural killer cell of claim 1, wherein the exogenous mitochondria are delivered into the natural killer cell by centrifuging a composition where the exogenous mitochondria and the natural killer cell are mixed.

5. A pharmaceutical composition comprising the natural killer cell of claim 1 as an active ingredient.

6. The pharmaceutical composition of claim 5, wherein the composition is in a liquid or frozen form.

7. A method for treating cancer in a subject in need thereof, comprising a step of administering a pharmaceutical composition that contains the natural killer cell of claim 1 as an active ingredient to the subject.

8. The method of claim 7, wherein the composition is administered via a route selected from the group consisting of intravenous, subcutaneous, ophthalmic, intraperitoneal, and intramuscular routes.

9. The method of claim 7, wherein the method comprises administering to the subject another drug or physiologically active substance having an effect of treating cancer in combination with the natural killer cell.

10. The method of claim 7, wherein the cancer is selected from the group consisting of gastric cancer, liver cancer, lung cancer, colorectal cancer, breast cancer, prostate cancer, ovarian cancer, pancreatic cancer, cervical cancer, thyroid cancer, laryngeal cancer, acute myelogenous leukemia, brain tumor, neuroblastoma, retinoblastoma, head and neck cancer, salivary gland cancer, and lymphoma.

11. A method for treating an infectious disease in a subject in need thereof, comprising a step of administering a pharmaceutical composition that contains the natural killer cell of claim 1 as an active ingredient to the subject.

12. The method of claim 11, wherein the infectious disease is selected from the group consisting of hepatitis B, hepatitis C, human papilloma virus (HPV) infection, cytomegalovirus infection, viral respiratory disease, and influenza.

13. The method of claim 11, wherein the composition is administered via a route selected from the group consisting of intravenous, subcutaneous, ophthalmic, intraperitoneal, and intramuscular routes.

14. The method of claim 11, wherein the method comprises administering to the subject another drug or physiologically active substance having an effect of treating the infectious disease in combination with the cell.

* * * * *